(12) United States Patent
Kim

(10) Patent No.: US 11,491,340 B2
(45) Date of Patent: Nov. 8, 2022

(54) SKIN TREATMENT APPARATUS USING FRACTIONAL PLASMA

(71) Applicant: SEOULIN MEDICARE CO., LTD., Hwaseong-si (KR)

(72) Inventor: Byoung Choul Kim, Seongnam-si (KR)

(73) Assignee: SEOULIN MEDICARE CO., LTD., Hwaseong-si (KR)

( * ) Notice: Subject to any disclaimer, the term of this patent is extended or adjusted under 35 U.S.C. 154(b) by 573 days.

(21) Appl. No.: 16/500,936

(22) PCT Filed: Feb. 1, 2018

(86) PCT No.: PCT/KR2018/001361
§ 371 (c)(1),
(2) Date: Oct. 4, 2019

(87) PCT Pub. No.: WO2018/190499
PCT Pub. Date: Oct. 18, 2018

(65) Prior Publication Data
US 2020/0069957 A1    Mar. 5, 2020

(30) Foreign Application Priority Data
Apr. 12, 2017 (KR) .......................... 10-2017-0047276

(51) Int. Cl.
*A61N 1/44* (2006.01)
*H05H 1/24* (2006.01)

(52) U.S. Cl.
CPC ............ *A61N 1/44* (2013.01); *H05H 1/2406* (2013.01); *H05H 2277/10* (2013.01)

(58) Field of Classification Search
None
See application file for complete search history.

(56) References Cited

U.S. PATENT DOCUMENTS 10,692,704 B2 *  6/2020  Louis ................ H01J 37/32348
11,102,877 B2 *  8/2021  Eckert .................. H05H 1/2406
(Continued)

FOREIGN PATENT DOCUMENTS

KR    10-2013-0106017 A    9/2013
KR      10-1422823 B1      8/2014
(Continued)

*Primary Examiner* — Srinivas Sathiraju
(74) *Attorney, Agent, or Firm* — Rabin & Berdo, P.C.

(57) ABSTRACT

The present invention relates to a skin treatment apparatus using fractional plasma, in which a plasma generator includes an electrode plate, a dielectric body, a pin holder, a plurality of pins, and a gap maintaining part and further includes a lower support which includes a pin cover, vents, and an auxiliary gap maintaining part. According to the present invention, the plurality of pins are configured as independent electrodes to prevent concentration of plasma, ends of the plurality of pins are pointed to more smoothly generate plasma, the distances between the plurality of pins may be more reliably maintained using the pin cover, plasma generated by the plurality of pins may be evenly emitted onto the skin via the pin cover and vents without being concentrated on a curved region of the skin, and the auxiliary gap maintaining part moves in a vertical direction of the gap maintaining part to adjust a distance between the plurality of pins and the skin.

4 Claims, 5 Drawing Sheets

(56) References Cited

U.S. PATENT DOCUMENTS

| | | | |
|---|---|---|---|
| 11,167,125 B2* | 11/2021 | Moss | A61B 34/37 |
| 2002/0161362 A1* | 10/2002 | Penny | H05H 1/24 |
| | | | 606/41 |
| 2003/0120269 A1* | 6/2003 | Bessette | A61B 18/1815 |
| | | | 606/32 |
| 2005/0119605 A1* | 6/2005 | Sohn | A61M 37/00 |
| | | | 604/21 |
| 2006/0084158 A1* | 4/2006 | Viol | A61L 2/14 |
| | | | 435/173.1 |
| 2006/0265034 A1* | 11/2006 | Aknine | A61B 18/18 |
| | | | 607/101 |
| 2008/0312579 A1* | 12/2008 | Chang | A61N 1/0412 |
| | | | 264/129 |
| 2009/0043247 A1* | 2/2009 | Kreindel | A61B 18/14 |
| | | | 604/21 |
| 2009/0287208 A1* | 11/2009 | Rosemberg | A61N 1/0448 |
| | | | 606/43 |
| 2009/0299361 A1* | 12/2009 | Flyash | A61N 5/00 |
| | | | 606/33 |
| 2010/0179455 A1* | 7/2010 | Nebrigic | A61B 18/18 |
| | | | 606/33 |
| 2010/0296977 A1* | 11/2010 | Hancock | A61L 2/02 |
| | | | 422/186 |
| 2012/0150098 A1* | 6/2012 | Etheredge | A61N 1/30 |
| | | | 604/20 |
| 2012/0277659 A1* | 11/2012 | Yaroslavsky | A61B 18/203 |
| | | | 604/20 |
| 2013/0345620 A1* | 12/2013 | Zemel | A61B 18/042 |
| | | | 604/24 |
| 2014/0316393 A1* | 10/2014 | Levinson | A61B 18/02 |
| | | | 606/41 |
| 2016/0271419 A1* | 9/2016 | Varghese | A61B 18/042 |
| 2017/0043150 A1* | 2/2017 | Kim | A61H 23/0218 |
| 2017/0325992 A1* | 11/2017 | DeBenedictis | A61K 9/0014 |
| 2017/0326347 A1* | 11/2017 | Kalghatgi | A61B 18/042 |
| 2017/0339776 A1* | 11/2017 | Knoll | H05H 1/48 |
| 2017/0348539 A1* | 12/2017 | Schwarz | A61N 1/328 |
| 2018/0130646 A1* | 5/2018 | Louis | B01J 19/1887 |
| 2018/0236226 A1* | 8/2018 | Na | A61N 1/05 |
| 2019/0015673 A1* | 1/2019 | Masic | A61B 5/015 |
| 2019/0053365 A1* | 2/2019 | Kim | A61B 5/441 |
| 2019/0083161 A1* | 3/2019 | Harle | H05H 1/3405 |
| 2019/0090339 A1* | 3/2019 | Frame | A61B 18/042 |
| 2019/0134414 A1* | 5/2019 | Prouza | A61N 1/403 |
| 2019/0217080 A1* | 7/2019 | Moss | A61B 18/1402 |
| 2020/0069957 A1* | 3/2020 | Kim | A61N 1/44 |
| 2020/0206072 A1* | 7/2020 | Capelli | A61B 18/203 |
| 2021/0076813 A1* | 3/2021 | Wandke | A61N 1/44 |
| 2021/0370049 A1* | 12/2021 | Moss | A61N 1/40 |
| 2022/0126096 A1* | 4/2022 | Claude | A61N 1/36034 |

FOREIGN PATENT DOCUMENTS

| | | |
|---|---|---|
| KR | 10-1568380 B1 | 11/2015 |
| KR | 10-2016-0111119 A | 9/2016 |

* cited by examiner

[FIG 1]
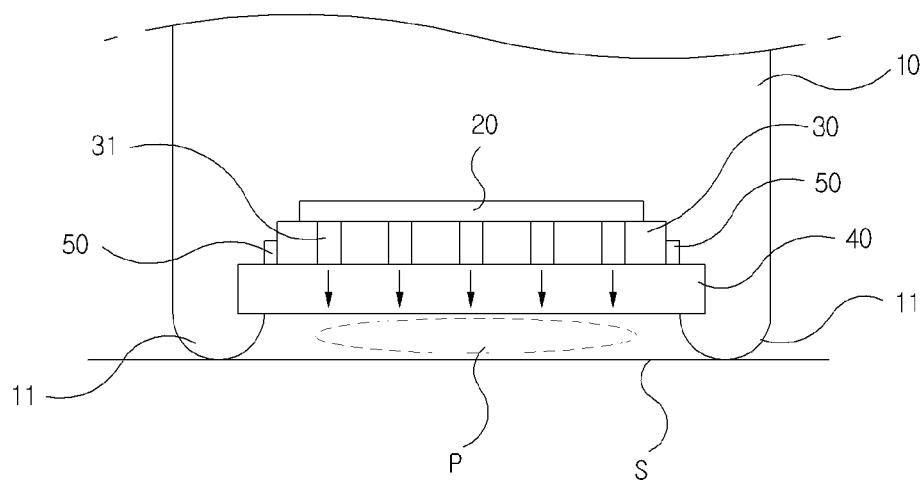
[FIG 2]
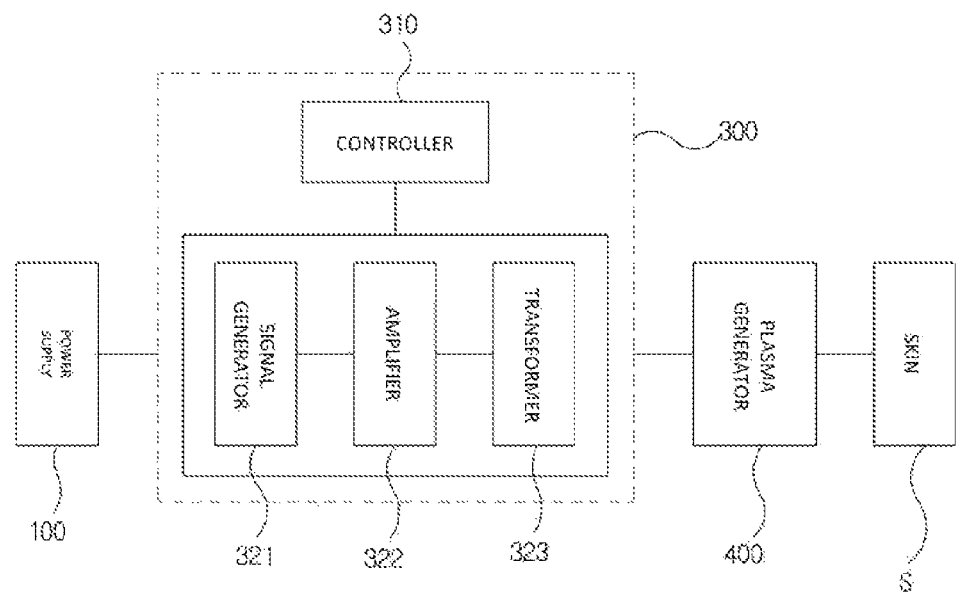

[FIG 3]
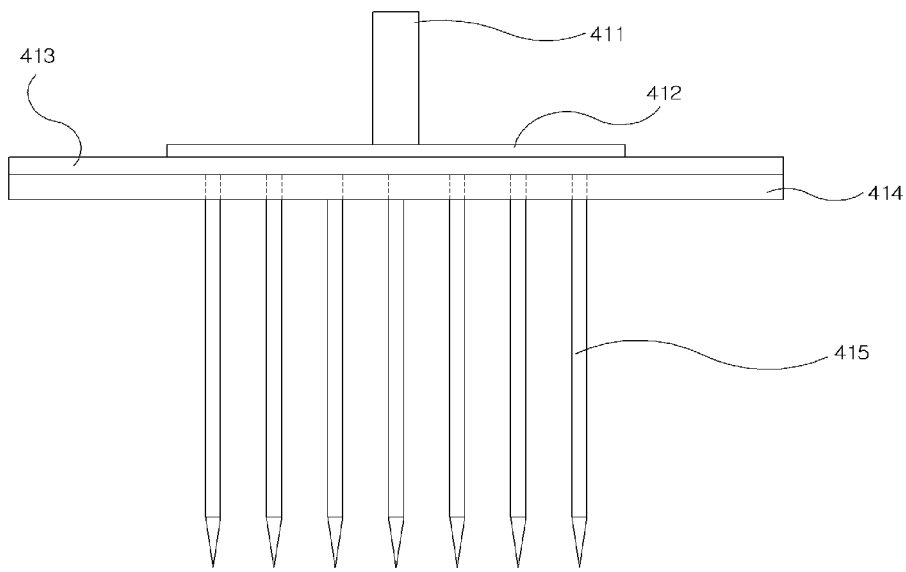
[FIG 4]
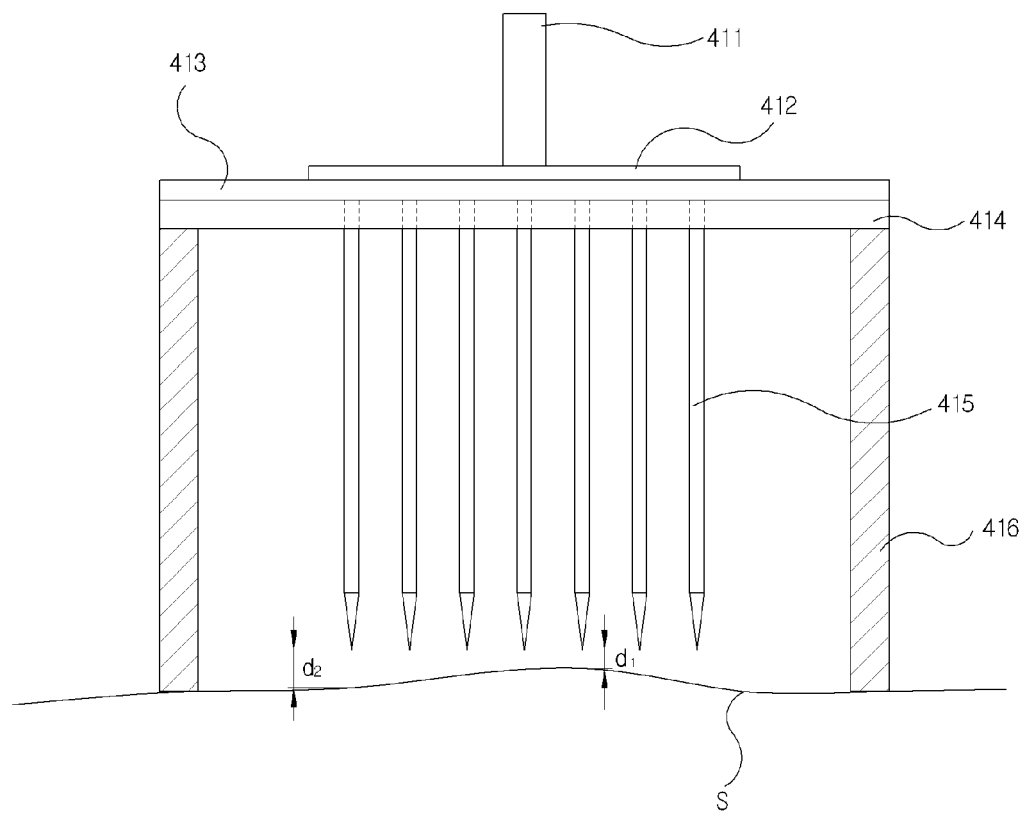

[FIG 5]
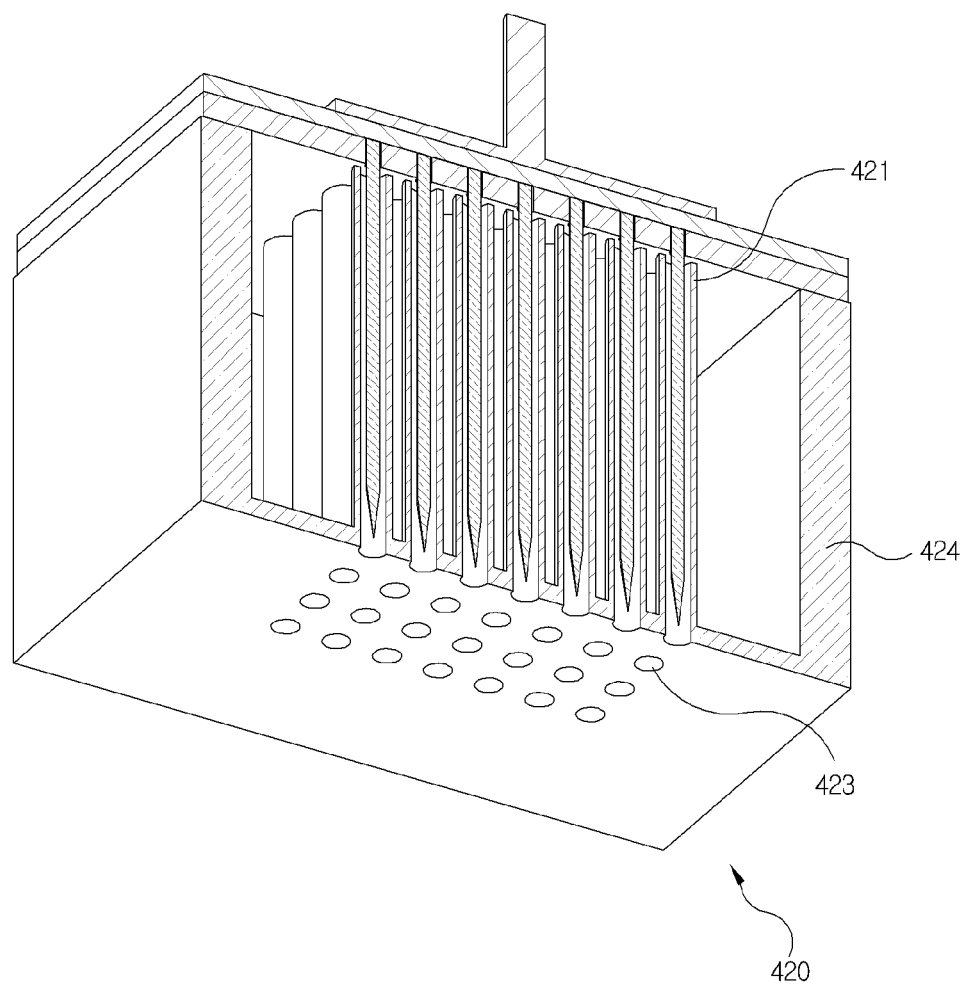

[FIG 6]
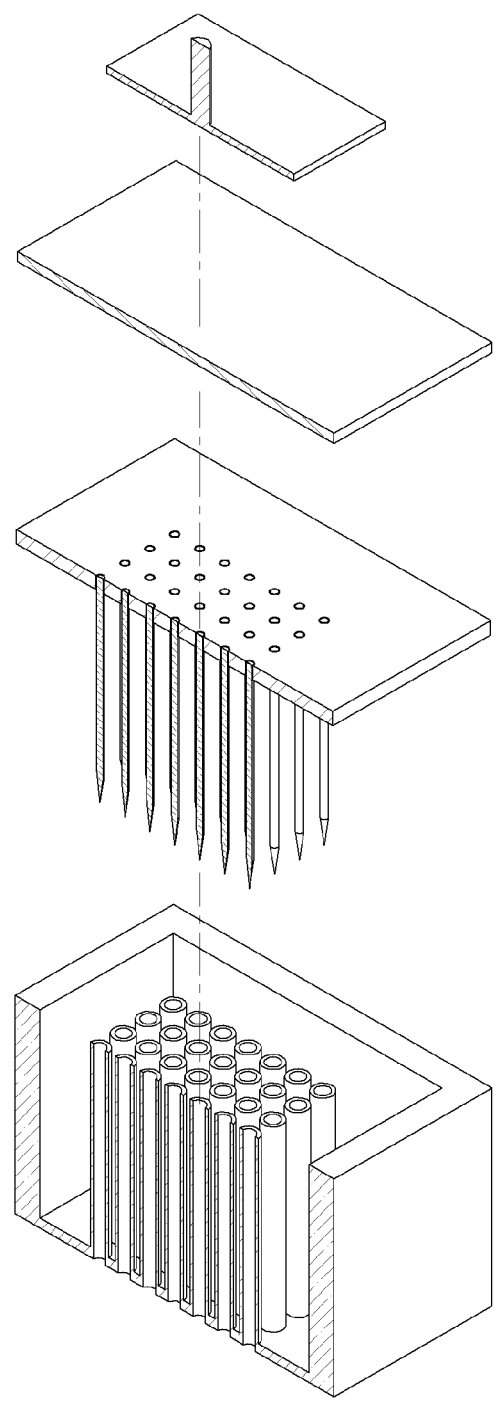

[FIG 7]
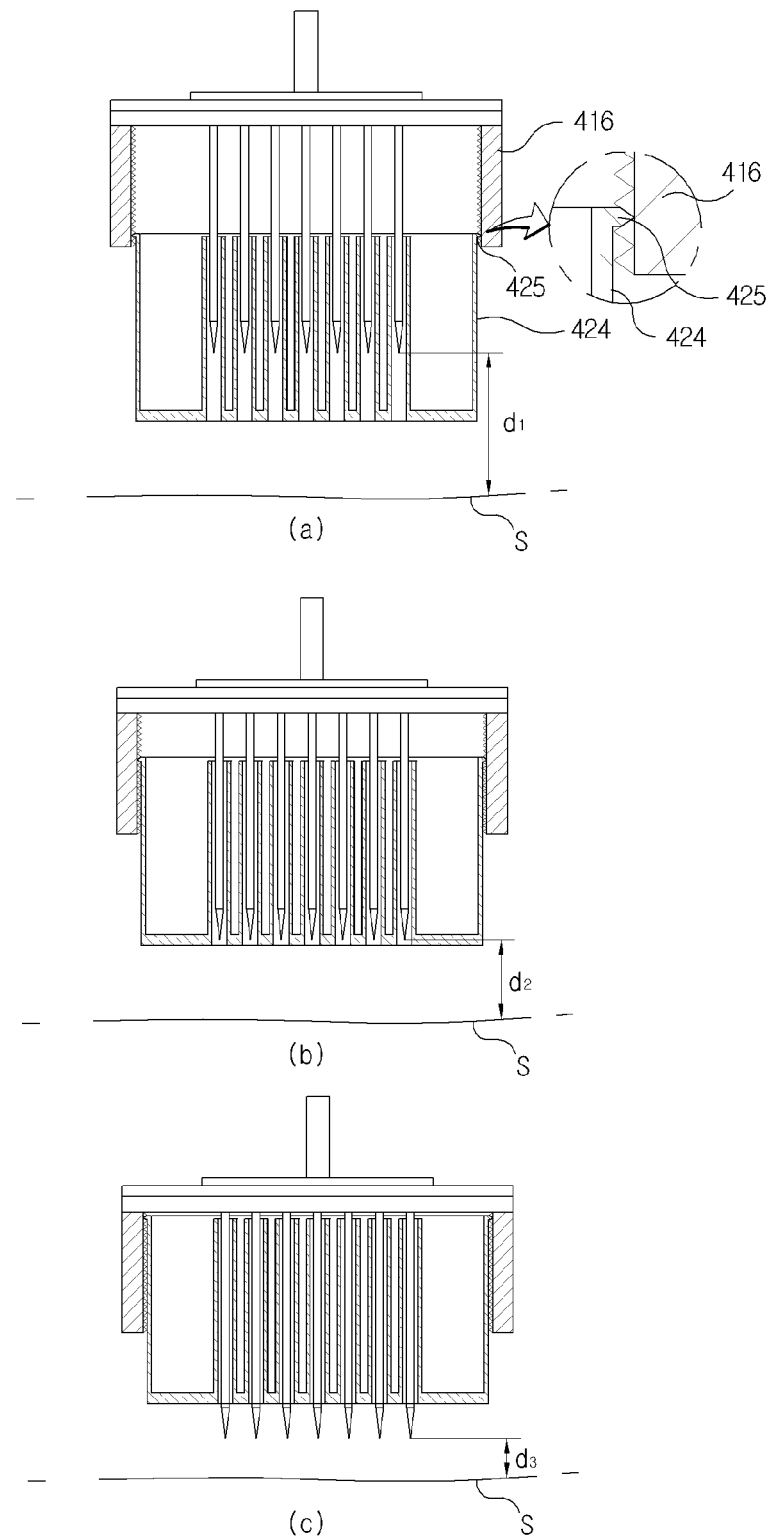

SKIN TREATMENT APPARATUS USING FRACTIONAL PLASMA

CROSS REFERENCE TO RELATED APPLICATIONS

This application is a National Phase filing under 35 U.S.C. § 371 of PCT/KR2018/001361 filed on Feb. 1, 2018; which application in turn claims priority to Application No. 10-2017-0047276 filed in Korea on Apr. 12, 2017. The entire contents of each application are hereby incorporated by reference.

TECHNICAL FIELD

The present invention relates to a skin treatment apparatus using fractional plasma, and more particularly, to a skin treatment apparatus using fractional plasma, in which a dielectric body is provided to generate soft plasma by inducing a dielectric barrier discharge to occur between the skin and a plasma generator, and a plurality of pins are configured as independent electrodes to prevent concentration of plasma.

BACKGROUND ART

A state of a material may be divided into a solid state, a liquid state, and a gaseous state. When energy is applied to a gaseous material, electrons are separated from atoms or molecules to cause a plasma state in which electrons, ions, and neutral particles (molecules and atoms) are mixed.

In the plasma state, the electrons can be easily accelerated in various ways, the neutral particles may collide with molecules of a material to be processed to produce chemically active species, and the ions form conditions causing chemical reactions to occur at a surface of the material to be processed so that the active species may cause an active chemical action on the surface of the material.

That is, the plasma contains, for example, chemically active species, such as oxy-, hydroxyl-, and nitrogen radicals, electronically excited atoms or molecules, and ultraviolet (UV) photons, ions, and radicals, which lightly and gently tap an affected area to stimulate and sterilize the affected area, as if the affected area is showered, while moving along an electric field.

Plasma is easier to generate in a low-pressure vacuum state of about 1 mTorr to 100 Torr than at atmospheric pressure. However, in order to generate plasma at such low pressures, there are various constraints, e.g., it is necessary to manufacture a vacuum container and attach a vacuum pump thereto to maintain a vacuum. For this reason, much research has been conducted on a method of generating plasma under atmospheric pressure other than a vacuum state, and thus, recently, plasma has been generated under pressure equal to or greater than the atmospheric pressure.

With characteristics of plasma and the development of a generation method thereof, plasma has been used in various fields of industry. Many practical attempts have been made to use a plasma technique in medical fields such as sterilization of micro-organisms, hemostasis of wounds, teeth whitening, and killing cancer cells. In particular, a technique for using plasma for skin treatment has been shown to have potential earlier than other fields, and in-depth research has been conducted thereon.

Plasma may be classified into a thermal plasma discharge and a non-thermal plasma discharge according to a method of generating plasma. The thermal plasma discharge is a method of ionizing a gas by heat, and the non-thermal plasma method is a method of ionizing a gas by mainly heating electrons while minimizing heating of the gas. The non-thermal plasma discharge method is also referred to as non-equilibrium plasma method, because only electrons have a high temperature but remaining ions and neutral particles are maintained at low temperatures, thereby causing thermal unbalance.

Non-thermal plasma is generated by the following process. When two planar conductors are separated from each other by a distance d and a voltage V is applied thereto, an electric field E is generated under a condition of $E=V/d$. In this case, when the voltage V reaches a certain level or higher, charged particles (electrons) are accelerated by the electric field E, are provided with energy, and thus collide with neutral gas atoms or molecules. Thus, atoms and molecules are ionized to a plasma state in which electrons, ions, and neutral particles (molecules and atoms) are mixed.

In the plasma generator of the related art (KR10-1568380 B1), as illustrated in FIG. 1, a plasma generator is provided in the form of a tip at the end of a cylindrical housing 10 of a handpiece type and includes an electrode 20 to which a frequency is applied from a transformer, a disc-shaped substrate 30 located on a lower surface of the electrode 20 and having a plurality of through-holes 31 vertically formed at uniform intervals to be in contact with the electrode 20, and a dielectric body 40 in contact with a lower surface of the substrate 30.

The through-holes 31 are formed in the substrate 30, similar to the shape of holes of a shower, and the inner surface thereof may be coated or plated with a conductive material. The dielectric body 40 may be formed of a material such as quartz, sapphire, glass, ceramic, or polymer film, and have a thickness in a range of about 0.1 mm to 3 mm and a relative dielectric constant in a range of about 4 to 18.

Therefore, power is delivered from the electrode 20 to the dielectric body 40 via through the through-holes 31 of the substrate 30 in a manner similar to a shower manner, and thus, an R-L-C series circuit is formed between the dielectric body 40 and skin S so that the skin S may be in the form of circuit having a low impedance and thus a weak current that does not harm the human body may flow through the skin S. In this case, plasma P is generated between the skin S and the dielectric body 40 which are in contact with each other by a gentle dielectric barrier discharge based on a plasma shower method.

However, according to the related art, a high frequency and high voltage are applied to the electrode 20 and power is transferred from the electrode 20 to the dielectric body 40 via the through-holes 13 of the substrate 30 in a manner similar to a shower manner, thereby generating plasma between the dielectric body 40 and the skin S. Because all the through-holes 13 are connected to one electrode 20, the through-holes 13 cannot operate as independent electrodes and thus the plasma may be unevenly generated in the through-holes 13, i.e., a plasma concentration phenomenon may occur.

Furthermore, a dielectric body is disposed between an electrode and the skin tissue to limit current and thus smooth plasma may be generated, but sufficient plasma cannot be generated.

In addition, in the related art, the distance between a point at which plasma starts to be generated and the skin is fixed and thus cannot be adjusted by a user.

DISCLOSURE

Technical Problem

To address the above-mentioned problems, the present invention is directed to providing a skin treatment apparatus using fractional plasma, which includes an electrode plate, a dielectric body, a pin holder, and a plurality of pins and is capable of generating plasma from a voltage applied to the electrode plate using the dielectric body and the plurality of pins.

The present invention is also directed to providing a skin treatment apparatus using fractional plasma, in which a plurality of pins located below a dielectric body have pointed ends to generate plasma.

The present invention is also directed to providing a skin treatment apparatus using fractional plasma in which a gap maintaining part and an auxiliary gap maintaining part are provided and the auxiliary gap maintaining part moves in a direction perpendicular to the gap maintaining part.

Technical Solution

One aspect of the present invention provides a skin treatment apparatus for skin treatment using plasma generated by a plasma generator, wherein the plasma generator includes an electrode plate connected to the high-voltage module; a dielectric body below the electrode plate; a pin holder below the dielectric body; and a plurality of pins, one end of each of which is disposed at a bottom of the dielectric body at a regular interval and which are configured to independently operate and pass through the pin holder, and power is supplied from the electrode plate to the dielectric body and the plurality of pins so as to generate plasma in a space between another end of each of the plurality of pins and the skin.

In the skin treatment apparatus using fractional plasma of the present invention, a gap maintaining part may protrude from a side of the plasma generator toward the skin to maintain a distance between the other ends of the plurality of pins and the skin.

In the skin treatment apparatus using fractional plasma of the present invention, the gap maintaining part may be installed along an outer circumferential surface of the pin holder of the plasma generator.

In the skin treatment apparatus using fractional plasma of the present invention, the plasma generator may further include a hollow lower support with an open upper surface, wherein the lower support may include pin covers formed in a hollow shape inside the lower support to cover outer circumferential surfaces of the plurality of pins, the pin cover protruding toward the pin holder; vents provided below the lower support to communicate with the pin covers; and an auxiliary gap maintaining part provided at a side of the lower support to protrude toward the pin holder, and plasma generated by ends of the plurality of pins may pass through the pin covers and the vents and then be emitted toward the skin.

In the skin treatment apparatus using fractional plasma of the present invention, the plasma generator may further include a hollow lower support with an open upper surface, wherein the lower support may include pin covers formed in a hollow shape inside the lower support to cover outer circumferential surfaces of the plurality of pins, the pin cover protruding toward the pin holder; vents provided below the lower support to communicate with the pin covers; and an auxiliary gap maintaining part provided at a side of the lower support to protrude toward the pin holder, and plasma generated by ends of the plurality of pins may pass through the pin covers and the vents and then be emitted toward the skin.

In the skin treatment apparatus using fractional plasma of the present invention, the auxiliary gap maintaining part may move along a side of the gap maintaining part and in a vertical direction of the gap maintaining part.

Advantageous Effects

According to the present invention, a plurality of pins are provided as independent electrodes below a dielectric body to prevent concentration of plasma, ends of the plurality of pins are pointed to more smoothly generate plasma, pin covers covering outer circumferential surfaces of the pins are provided to more reliably maintain the distances between the plurality of pins, vents for communication with the pin covers are provided on a lower support to disperse plasma without being concentrated, a gap maintaining part is provided to maintain a distance between the pins and the skin, and an auxiliary gap maintaining part is provided to adjust a distance between the pins and the skin.

DESCRIPTION OF DRAWINGS

FIG. 1 illustrates a skin treatment apparatus using plasma according to the related art.

FIG. 2 is a block diagram illustrating an overall structure of the present invention.

FIG. 3 is a diagram illustrating main components of a plasma generator according to the present invention.

FIG. 4 is a view of a gap maintaining part included in the plasma generator according to the present invention.

FIG. 5 illustrates a state in which pins are surrounded by pin covers in the plasma generator according to the present invention.

FIG. 6 is an exploded perspective view of FIG. 5.

FIG. 7 is a diagram illustrating a vertical movement of an auxiliary gap maintaining part along the gap maintaining part in the plasma generator according to the present invention.

MODES OF THE INVENTION

Hereinafter, exemplary embodiments of the present invention will be described in more detail with reference to the accompanying drawings.

As illustrated in FIG. 2, a skin treatment apparatus using plasma according to the present invention includes a power supply 100, a high-voltage module 300, and a plasma generator 400. The high-voltage module 300 includes a controller 310, a signal generator 321, an amplifier 322, and a transformer 323.

The power supply 100 may be an external power source or may be a small-sized portable battery.

The controller 310 of the high-voltage module 300 controls direct-current (DC) power output from the power supply 100 to be converted into high-frequency and high-voltage alternating-current (AC) power. The signal generator 321 of the high-voltage module 300 generally generates a frequency of 20 kHz or more. The amplifier 322 of the high-voltage module 300 is matched with impedance in a range of 5 to 50 W.

The transformer 323 of the high-voltage module 300 supplies the frequency output from the amplifier 322 of the high-voltage module 300 to the plasma generator 400 to generate plasma.

FIG. 3 illustrates main components of the plasma generator 400 which generates plasma using high-voltage and high-frequency power output from the high-voltage module 300.

The plasma generator 400 includes a power connection part 411 for transmitting power from the transformer 323 of the high-voltage module 300, an electrode plate 412 to which high voltage and high frequency are applied via the power connection part 411, and a dielectric body 413 located below the electrode plate 412. A plurality of pins 415 protrude from a lower portion of the dielectric body 413 toward the skin S. A pin holder 414 is provided below the dielectric body 413 to support the plurality of pins 415.

FIG. 4 is a diagram illustrating that a gap maintaining part 416 is provided on a side of the plasma generator according to the present invention. The gap maintaining part 416 is configured to maintain a constant distance between pins and the skin.

FIG. 5 illustrates that the pin 415 is covered with a pin cover 421. The pin cover 421 is formed in a hollow shape. One end of the pin cover 421 is supported on an inner lower end of a hollow lower support 420 with an open upper surface, and another end thereof is spaced a certain distance apart from the pin holder 414.

The pin covers 421 are connected to a vent 423 of the lower support 420.

An auxiliary gap maintaining part 424 protrudes from a side of the lower support 420 toward the pin holder 414.

FIG. 7 is a diagram illustrating a vertical movement of the auxiliary gap maintaining part 424 along the gap maintaining part 416 in the plasma generator according to the present invention.

The skin treatment apparatus using plasma according to the present invention configured as described above operates as described below.

In the present invention, a skin treatment process will be described taking an example of application to skin with acne.

First, when a skin treatment device of the present invention is placed on a region of the skin with acne to be treated and a start button is pressed, the power supply 100 supplies DC power to the high-voltage module 300, and the high-voltage module 300 converts the DC power into high-voltage and high-frequency AC power via the controller 310, the signal generator 321, the amplifier 322, and the transformer 323 and supplies the AC power to the electrode plate 412 via the power connection part 411 of the plasma generator 400.

The electrode plate 412 may be formed of a conductive material such as gold, silver, or copper.

The power supplied to the electrode plate 412 passes through the dielectric body 413. The dielectric body 413 may be glass, plastic, ceramic, silicon, quartz, or the like. Due to the dielectric body 413 formed of such a material, an arc discharge, which is a plasma discharge, is prevented from occurring to prevent damage to the human body (skin).

In addition, plasma P is generated between the skin S and the pins 415 protruding from the lower portion of the dielectric body 413 toward the skin S. The plurality of pins 415 are provided and supported on the pin holder 414.

Because the plurality of pins 415 are not directly connected to the electrode plate 412 but are connected to the dielectric body 413, the plurality of pins 415 may operate as independent electrodes to prevent concentration of plasma and to uniformly generate plasma by each of the plurality of pins 415.

In addition, the plurality of pins 415 facilitate a discharge, thereby smoothly generating plasma. One end of each of the plurality of pins 415 is supported by the pin holder 414 and another end thereof facing the skin may be formed to be pointed to smoothly generate plasma.

A plasma generator according to the present invention may include a gap maintaining part 416 as described with reference to FIG. 4 above.

The plasma generator of the present invention may not be provided with a gap maintaining part and may be used in a state in which the plurality of pins 415 protrude from the lower portion of the dielectric body 413 (see FIG. 3). In this state, a region of the skin to be treated may be treated by a user by freely moving the skin treatment apparatus around the region of the skin.

In addition, a user may need to treat the skin while the skin treatment apparatus of the present invention is fixed on the skin. In this case, when the gap maintaining part 416 is provided on a side of the plasma generator, treatment may be performed even when the skin treatment apparatus is fixed on the skin, and the skin treatment apparatus may be spaced a distance d2 even from a lower portion of a curved region of the skin and spaced a distance d1 even from a higher portion of the curved region of the skin to achieve a more stable electric field according to E=V/d, thereby more safely conducting a treatment using plasma.

A plasma generator according to the present invention may operate according to the above configuration and may be additionally combined with the lower support 420 with the pin cover 421 to treat the skin more effectively. This process will be described with reference to FIG. 5 below.

The pin cover 421 has a hollow shape and surrounds the outer circumferential surface of the pin 415. One end of the pin cover 421 in a lengthwise direction is spaced a certain distance apart from the pin holder 414 and another end thereof is connected to an inner lower portion of the lower support 420.

The pin covers 421 are configured to more reliably maintain a constant gap between the plurality of pins 415.

Plasma generated from ends of the pins 415 is emitted onto the skin via the pin covers 421 and the vents 423. In such a structure, plasma generated from a plurality of pins is transmitted along vents connected to respective pin covers, thereby increasing an effect of dispersing the plasma (see FIG. 5).

The plasma generator according to the present invention is capable of adjusting the gaps between the pins 415 and the skin using the auxiliary gap maintaining part 424 of the lower support to adjust the amount of plasma to be generated.

The auxiliary gap maintaining part 424 may move in the vertical direction along a side of the gap maintaining part 416 to adjust the gap between the pins and the skin.

The gap maintaining part includes a plurality of V-shaped grooves, and an engaging part 425 protruding from the auxiliary gap maintaining part 424 toward the gap maintaining part may move along the grooves of the gap maintaining part to adjust the gaps between the pins and the skin.

FIG. 7A illustrates a case in which a distance d1 between the pins and the skin is large because the engaging part 425 of the auxiliary gap maintaining part 424 is connected to a lower end of the gap maintaining part 416.

FIG. 7B illustrates a case in which a distance d2 between the pins and the skin is intermediate because the engaging part 425 of the auxiliary gap maintaining part 424 is connected to a middle portion of the gap maintaining part 416.

FIG. 7C illustrates a case in which a distance d3 between the pins and the skin is very small because the engaging part 425 of the auxiliary gap maintaining part 424 is connected to an upper end of the gap maintaining part 416 and thus ends of the pins protrude toward an outer side of the lower support.

A skin treatment apparatus using plasma according to the present invention described above is not limited to the above embodiments, and various modifications may be made therein by those of ordinary skill in the art without departing from the technical scope claimed in the following claims.

The invention claimed is:

1. A skin treatment apparatus using fractional plasma, comprising:
   a high-voltage module; and
   a plasma generator,
   wherein the skin treatment apparatus conducts skin treatment using plasma generated by the plasma generator,
   the plasma generator comprises:
   an electrode plate connected to the high-voltage module;
   a dielectric body below the electrode plate;
   a pin holder below the dielectric body; and
   a plurality of pins, one end of each of which is disposed at a bottom of the dielectric body at a regular interval, the plurality of pins configured to independently operate and pass through the pin holder, and
   power is supplied from the electrode plate to the dielectric body and the plurality of pins so as to generate plasma in a space between another end of each of the plurality of pins and skin SI
   wherein the plasma generator further comprises a hollow lower support with an open upper surface,
   wherein the lower support comprises:
   pin cover formed in a hollow shape inside the lower support to cover outer circumferential surfaces of the plurality of pins, the pin cover protruding toward the pin holder;
   vents provided below the lower support to communicate with the pin covers; and
   an auxiliary gap maintaining part provided at a side of the lower support to protrude toward the pin holder, and
   plasma generated by ends of the plurality of pins passes through the pin covers and the vents and then is emitted toward the skin S.

2. The skin treatment apparatus of claim 1, further comprising a gap maintaining part protruding from a side of the plasma generator toward the skin S to maintain a distance between the other end of each of the plurality of pins and the skin S.

3. The skin treatment apparatus of claim 2, wherein the gap maintaining part is installed along an outer circumferential surface of the pin holder of the plasma generator.

4. The skin treatment apparatus of claim 1, wherein the auxiliary gap maintaining part moves along a side of the gap maintaining part and in a vertical direction of the gap maintaining part.

* * * * *